(12) United States Patent
Hirama

(10) Patent No.: US 6,258,030 B1
(45) Date of Patent: Jul. 10, 2001

(54) ULTRASONIC DIAGNOSTIC APPARATUS

(75) Inventor: Makoto Hirama, Tochigi (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/516,379

(22) Filed: Mar. 1, 2000

(30) Foreign Application Priority Data

Mar. 11, 1999 (JP) .................................................. 11-065532

(51) Int. Cl.⁷ ........................................................ A61B 8/00
(52) U.S. Cl. ............................................. 600/443; 128/916
(58) Field of Search .................................... 600/443, 447, 600/448, 449, 437; 128/916

(56) References Cited

U.S. PATENT DOCUMENTS

| | | |
|---|---|---|
| 5,186,175 | 2/1993 | Hirama et al. . |
| 5,546,807 * | 8/1996 | Oxaal et al. ............................ 73/606 |
| 5,793,701 * | 8/1998 | Wright et al. ......................... 600/443 |
| 6,008,813 * | 12/1999 | Lauer et al. .......................... 345/424 |

* cited by examiner

Primary Examiner—Peter Vo
Assistant Examiner—Maulin Patel

(74) Attorney, Agent, or Firm—Oblon, Spivak, McClelland, Maier & Neustadt, P.C.

(57) ABSTRACT

The present invention discloses a three-dimensional ultrasonic diagnostic apparatus that makes it possible to reduce the cost of the apparatus and reduce power consumption by decreasing the number of delay circuits to be used for forming reception beams from reflection waves. An ultrasonic diagnostic apparatus of the present invention includes a three-dimensional ultrasonic scanning unit for carrying out a three-dimensional ultrasonic scanning by a plurality of ultrasonic transducers arranged two-dimensionally and for forming detection signals corresponding to reflection waves reflected from a subject that received waves applied by the transducers, a first delay add processing unit for dividing detection signal from all the transducers into a predetermined plurality of partial signal groups and for carrying out delay add processing to each of the divided partial signal groups to form a first delay adding signal, a second delay add processing unit for carrying out a delay add processing to the first delay adding signal output from the first delay add processing unit to form a second delay adding signal, and an image processing unit for reconstructing a three-dimensional image according to the second delay adding signal output from the second delay add processing unit. Based on this arrangement, it is possible to achieve a parallel simultaneous reception processing of a three-dimensional scanning with a small number of delay circuits. This facilitates a real-time display of the three-dimensional ultrasonic diagnostic apparatus.

13 Claims, 9 Drawing Sheets

ULTRASONIC DIAGNOSTIC APPARATUS

BACKGROUND OF THE INVENTION

1. Field of the Invention

The present invention relates to an ultrasonic diagnostic apparatus. The invention relates more particularly to a technique for reducing cost and power consumption of a three-dimensional diagnostic apparatus by decreasing the number of delay circuits used for forming reception beams, in the three-dimensional diagnostic apparatus for obtaining a real-time three-dimensional image by three-dimensionally scanning a human body by applying ultrasonic beams thereto.

2. Description of the Background Art (1) Two-dimensional ultrasonic diagnostic apparatus
Conventionally, there has been known an ultrasonic diagnostic apparatus for obtaining a two-dimensional tomogram of a subject such as a human body.

FIG. 1 shows a part of a conventional two-dimensional ultrasonic diagnostic apparatus. This two-dimensional ultrasonic diagnostic apparatus employs a one-dimensional array probe 101 having a plurality of fine transducers 100 arranged in one row as shown in FIG. 1.

The operation of the two-dimensional ultrasonic diagnostic apparatus will be explained below.

At the time of transmitting ultrasonic beams from the two-dimensional ultrasonic diagnostic apparatus, a transmission electric signal is supplied to each transducer 100 through a delay circuit provided for each transducer 100. When each transducer 100 has received this transmission electric signal, each transducer 100 is driven, and ultrasonic beams are being sent from the transducer 100. By changing the delay time of each delay circuit, beam directions to a focus F of the ultrasonic beams can be changed as shown by solid lines and a dotted line in FIG. 1. The conventional two-dimensional ultrasonic diagnostic apparatus is structured to scan a subject by the ultrasonic beams in a desired direction by arbitrarily changing the delay time set in each delay circuit.

On the other hand, at the time of receiving ultrasonic beams in the two-dimensional ultrasonic diagnostic apparatus, each transducer 100 detects a reflection wave (echo) reflected from the focus F.

FIG. 2 shows a structure of the two-dimensional ultrasonic diagnostic apparatus. Each detection signal detected by the transducer 100 is delay processed with a predetermined delay time by a delay circuit 102 shown in FIG. 2. By this delay processing, phases of the detection signals corresponding to the focus F are matched. The detection signals after the phase matching are added together by an adder circuit 103 to be formed as a reception signal. This signal is then supplied to an image processing circuit. The image processing circuit executes a predetermined image processing to reception signals to reconstruct a two-dimensional tomogram and displays it in a display. With the above-described processing, it is possible to obtain a two-dimensional tomogram of a subject. The above-described two-dimensional ultrasonic diagnostic apparatus requires the delay circuits 102 by the number of the transducers 100 for simultaneously receiving reflection waves. These delay circuits are combined with the ultrasonic transducers to converge the ultrasonic beams into the focus F, and at the same time, controls the scanning direction of the ultrasonic beams and directivity of each transducer as a sensor.

Next, according to the conventional ultrasonic diagnostic apparatus, there has been put into practical use a so-called real-time display for displaying images obtained in real time from ultrasonic waves. To achieve this real-time display, it is necessary to display images of 10 to 30 frames every second. For reconstructing these large number of frame images, there is required information of a large number of scanning lines that comprise the frames. As one of methods for a real-time display, there is "parallel simultaneous reception processing". This parallel simultaneous reception processing is a method for obtaining information of a plurality of scanning lines in one-time transmission of ultrasonic wave. To be more specific, a plurality of scanning lines whose directivity mutually differ are set within the ultrasonic wave to be transmitted, and a plurality of reception signals along these scanning lines are formed, synthesized and signal-processed thereby so as to reconstruct ultrasonic tomographic images on the plurality of scanning lines.

FIG. 3 shows a structure of the two-dimensional ultrasonic diagnostic apparatus for carrying out the parallel simultaneous reception processing. Steps of the parallel simultaneous reception processing will be explained with reference to FIG. 3.

In the parallel simultaneous reception processing, a plurality of delay circuits 102 are provided in one reception channel 105 corresponding to one transducer 100 as shown in FIG. 3. By setting different delay times for these delay circuits 102, a plurality of detection signals with different phases are formed. Next, of the detection signals from the delay circuits 102 of the respective reception channels 105, detection signals of the same phase are added together by the adder circuit 103, so that a plurality of reception signals are formed. By reconstructing these reception signals, one ultrasonic tomographic image is obtained.

The above-described parallel simultaneous reception processing requires the delay circuits as follows:

the number of delay circuits=the number of the transducers×the number of parallel simultaneous receptions In this case, the number of ultrasonic transducers is equal to the number of reception channels. The number of parallel simultaneous receptions is equal to the number of scanning lines per one reception channel.

In general, the number of reception channels held by the two-dimensional ultrasonic diagnostic apparatus is about 100, while the number of parallel simultaneous reception is about four. Accordingly, the number of delay circuits required by the two-dimensional ultrasonic diagnostic apparatus is:

100 channels×4=about 400

(2) Three-dimensional ultrasonic diagnostic apparatus

A three-dimensional ultrasonic diagnostic apparatus will be explained next. There has been an attention focussed on the three-dimensional ultrasonic diagnostic apparatus in recent years. The three-dimensional ultrasonic diagnostic apparatus employs a two-dimensional array probe having a plurality of rows of array probes, each row having a plurality of transducers arranged in one row. With this two-dimensional array probe structure, a subject is scanned three-dimensionally by applying ultrasonic beams to obtain a three-dimensional image of the subject. Since this three-dimensional ultrasonic diagnostic apparatus has the array probe arranged two-dimensionally, it is necessary to process detection signals output from in excess of 1000 transducers. At the same time, the number of scanning lines required becomes enormous for reconstructing a three-dimensional image by carrying out a three-dimensional scanning.

Therefore, in the three-dimensional ultrasonic diagnostic apparatus, the above-described parallel simultaneous reception processing becomes inevitable for obtaining a plurality of scanning lines in one transmission, particularly in the case of carrying out a real-time display.

In this three-dimensional ultrasonic diagnostic apparatus, the number of delay circuits required for carrying out the above parallel simultaneous reception processing is obtained by the following formula, in a manner similar to that of the two-dimensional ultrasonic diagnostic apparatus:

the number of delay circuits=the number of the transducers×the number of parallel simultaneous receptions To be more specific, in the three-dimensional scanning, the two-dimensional array probe structure requires thereception channels by the number of at least 32 channels×32 channels, for reducing the artifact to a practical level. In this case, the number of the parallel simultaneous receptions becomes 4×4. Accordingly, the three-dimensional ultrasonic diagnostic apparatus requires an enormous large number of delay circuits obtained by the following formula:

32 channels×32 channels×4×4=16,384

Providing the above enormously large number of delay circuits in the three-dimensional ultrasonic diagnostic apparatus results in an increased manufacturing cost of the apparatus with an increase in power consumption and enlarging a scale of the apparatus.

As explained above, in the conventional three-dimensional ultrasonic diagnostic apparatus for carrying out a real-time display, there has been a problem of high manufacturing cost of the apparatus with large power consumption.

SUMMARY OF THE INVENTION

The present invention has been achieved with such points in view. It therefore is an object of the present invention to provide a three-dimensional ultrasonic diagnostic apparatus which makes it possible to achieve a cost reduction of the ultrasonic diagnostic apparatus and a reduction of power consumption, by decreasing the number of delay circuits necessary for carrying out a parallel simultaneous reception processing used for carrying out a real-time display of a three-dimensional image.

In order to achieve the above object, the present invention is characterized in that in a delay add processing including a parallel simultaneous reception processing necessary for carrying out a real-time display of a three-dimensional image, the delay add processing for forming reception beams is carried out by being divided into a plurality of stages.

In order to achieve the above function, there is provided an ultrasonic diagnostic apparatus, as shown in FIG. 4 and FIG. 5, for example, comprising: a three-dimensional ultrasonic scanning unit 2 for carrying out a three-dimensional ultrasonic scanning by a plurality of ultrasonic transducers arranged two-dimensionally and for forming detection signals corresponding to reflection waves reflected from a subject that received waves applied by the transducers; a first delay add processing unit 3 for dividing detection signal from all the transducers into a predetermined plurality of partial signal groups and for carrying out delay add processing to each of the divided partial signal groups to form a first delay adding signal; a second delay add processing unit 4 for carrying out a delay add processing to the first delay adding signal output from the first delay add processing unit to form a second delay adding signal; and an image processing unit 12 (shown in FIG. 5) for reconstructing a three-dimensional image based on the second delay adding signal output from the second delay add processing unit.

The first delay add processing unit 3 divides the detection signal groups from all the transducers 1 detected by the three-dimensional ultrasonic scanning unit 2, into a predetermined plurality of partial signal groups. The first delay add processing unit 3 and the second delay add processing unit 4 carry out delay add processing to each of the divided partial signal groups. Reception signals (reception beams) are formed by the plurality of stages of delay add processing. Since delay add processing is carried out to these partial detection signal groups, it is possible to decrease the number of delay circuits required.

The detection signal groups are divided into, for example, a row direction and a column direction of the transducers laid out in the two-dimensional array probe structure.

As a structure corresponding to this dividing method, it is preferable to provide an ultrasonic diagnostic apparatus, as shown in FIG. 4 and FIG. 5, for example, comprising: a three-dimensional ultrasonic scanning unit 2 for carrying out a three-dimensional ultrasonic scanning by a plurality of ultrasonic transducers arranged two-dimensionally and for forming detection signals corresponding to reflection waves reflected from a subject that received waves applied by the transducers; a first delay processing unit 3 for dividing detection signal groups from all the transducers into a plurality of partial signal groups in one direction of either a row direction or a column direction of the array of the transducers and for forming a plurality of signals in the one direction with mutually different phases for one reception channel from each of the divided partial signal groups; a first add processing unit 3 for adding detection signal groups of the same phase out of the detection signal groups output from the first delay processing section to form a first delay adding signal; a second delay processing unit 4 for forming a delay signal in another direction with mutually different phases for one reception channel, out of the first delay adding signal output from the first add processing unit; a second add processing unit 4 for forming a second delay adding signal by adding delay signal groups of the same phase out of the delay signals output from the second delay processing unit; and an image processing unit 12 (shown in FIG. 5) for reconstructing a three-dimensional image based on the second delay adding signal output from the second add processing unit.

The detection signal groups may also be divided into partial signal groups by at first collecting detection signals in the adjacent areas, for example.

As a structure corresponding to this dividing method, it is preferable to provide an ultrasonic diagnostic apparatus, as shown in FIG. 6 and FIG. 5, for example, comprising: a three-dimensional ultrasonic scanning unit 2 for carrying out a three-dimensional ultrasonic scanning by a plurality of ultrasonic transducers arranged two-dimensionally and for forming detection signals corresponding to reflection waves reflected from a subject that received waves applied by the transducers; a plurality of first delay processing units 20 for dividing detection signal groups from all the transducers into a plurality of partial signal groups in each adjacent area and for forming a plurality of signals with mutually different phases for one reception channel from each of the divided partial signal groups; a plurality of first add processing units 20 for adding detection signal groups of the same phase out of the detection signal groups output from the first delay processing section to form a first delay adding signal; a second delay processing unit 21 for forming a delay signal with mutually different phases for one reception channel, out of the first delay adding signal output from the first delay add processing section; a second add processing unit 21 for forming a second delay adding signal by adding delay signal groups of the same phase out of the delay signals output from the second delay processing section; and an image processing unit 12 (shown in FIG. 5) for reconstructing a three-dimensional image based on the second delay adding signal output from the second add processing unit.

According to the above three-dimensional ultrasonic diagnostic apparatus, the delay adding unit divides the reception signal groups from all the transducers of the three-dimensional ultrasonic scanning unit, into predetermined partial reception signal groups, and carries out a delay add processing for each of the divided partial reception signal groups. With this arrangement, the parallel simultaneous reception processing in the case of three-dimensional scanning can be achieved with a small number of delay circuits, and the real-time display of the three-dimensional ultrasonic diagnostic apparatus is facilitated.

Various further and more specific objects, features and advantages of the invention will appear from the description given below, taken in connection with the accompanying drawings illustrating by way of example a preferred embodiments of the invention.

BRIEF DESCRIPTION OF THE DRAWINGS

The accompanying drawings that are incorporated in and constitute a part of this specification, illustrate embodiments of the invention and, together with the description, serve to explain the principles of the invention.

DETAILED DESCRIPTION OF THE PREFERRED EMBODIMENTS

Embodiments of a three-dimensional ultrasonic diagnostic apparatus relating to the present invention will be explained in detail below with reference to the drawings.

First Embodiment

According to a first embodiment, there is provided a function for carrying out a delay add processing by dividing detection signals detected by ultrasonic transducers, into a row direction and a column direction.

Figure 4:
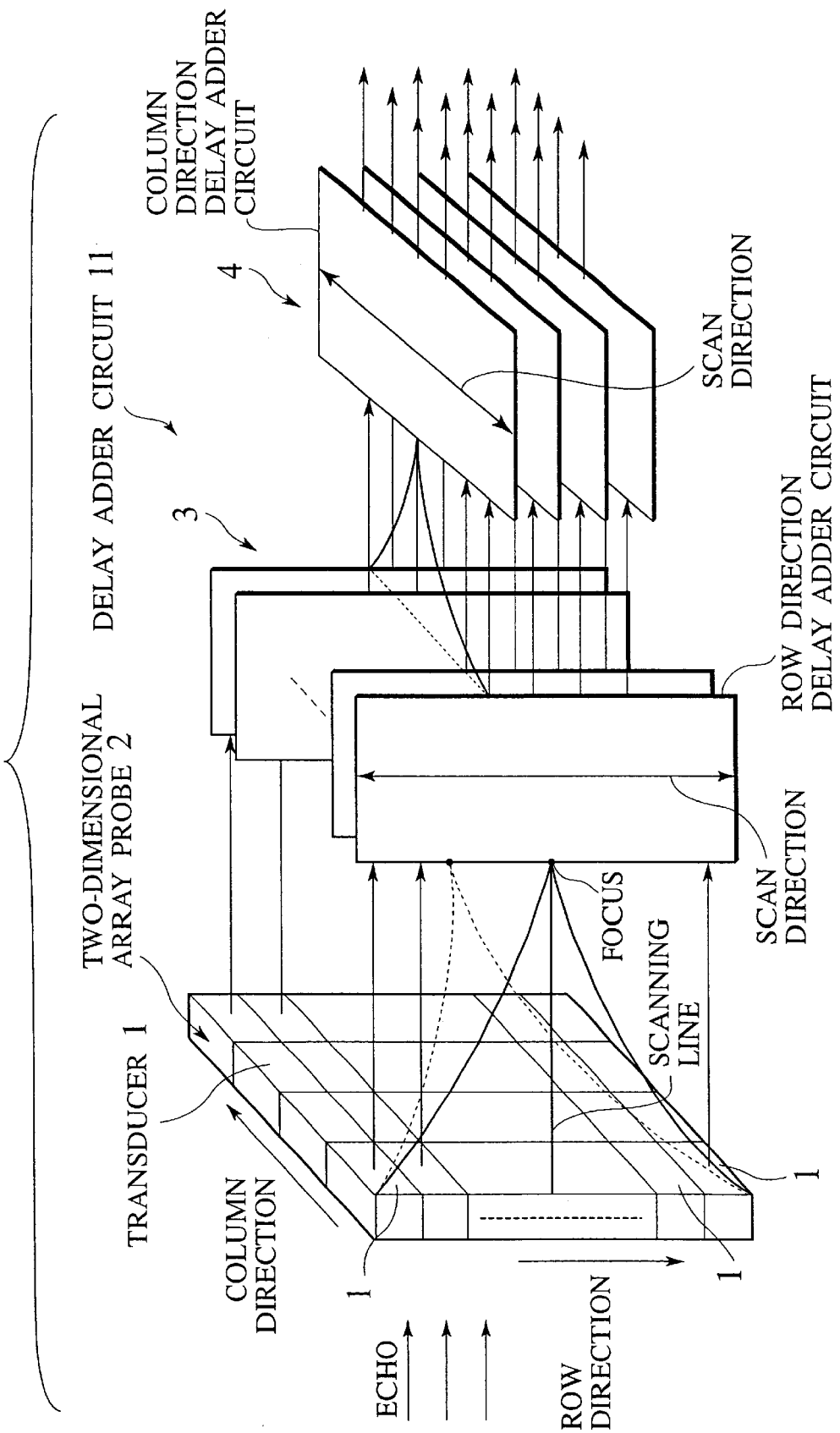
FIG. 4 is a view for explaining a configuration of a two-dimensional array probe and delay adder circuits of a three-dimensional ultrasonic diagnostic apparatus relating to a first embodiment of the present invention.

FIG. 4 shows a configuration of a three-dimensional ultrasonic diagnostic apparatus relating to the first embodiment of the present invention.

As shown in FIG. 4, the three-dimensional ultrasonic diagnostic apparatus relating to the first embodiment includes a two-dimensional array probe having a plurality of transducers 1 laid out in a row direction and a column direction, a row-direction delay adder circuit 3 for carrying out delay add processing in a row direction to detection signals detected by the transducers 1 in the row direction out of all the detection signals converted from ultrasonic reflection waves detected by each transducer 1 of the two-dimensional array probe 2 and for forming time-series signal groups, and column-direction delay adder circuit 4 for carrying out a delay add processing in a column direction to the time-series signal groups formed by the row direction delay adder circuits 3 and for forming reception signals based on three-dimensional scanning by the ultrasonic beams.

Unless otherwise explained, in the explanation hereinafter, the delay add processing is assumed to include above mentioned parallel simultaneous reception processing. The time-series signal groups consist of the group of the following number of signals per one column.

the number of transducers in row direction×the number of parallel simultaneous receptions in row direction.

In the row-direction delay adder circuit 3, a number K of parallel simultaneous receptions in a row direction is set at a value smaller than a number M of the transducers in one row for carrying out a reception processing of signals in the two-dimensional array probe 2. Similarly, in the row-direction delay adder circuit 4, a number L of parallel simultaneous receptions in a column direction is set at a value smaller than a number N of the transducers in one column for carrying out a reception processing of signals in the two-dimensional array probe 2.

The row-direction delay adder circuit 3 has units by the number of rows for generating delay adding signals in the row direction. Each unit converts each signal of M channels output from one row transducers into a plurality of delay adding signals of K parallel simultaneous receptions in a row direction per one signal.

Also, the row-direction delay adder circuit 3 determines a receiving scanning direction of scanning line viewed from a side direction, that is, viewed from a direction parallel with a column direction of the two-dimensional array probe 2 in FIG. 4. Arrow in the row-direction delay adder circuit 3 in FIG. 4 indicates a scanning direction in row direction. Here, scanning line is defined as a line connecting a focus with the center of corresponding row in the probe. In the row-direction delay adder circuit 3, a delay time for a reception signal from each transducer is set so that the scanning direction viewed from this side direction coincides with the scanning direction of each beam received simultaneously in the row direction.

The column-direction delay adder circuit 4 determines a scanning direction of scanning line viewed from the above, that is, viewed from a direction parallel with the row direction of the two-dimensional array probe 2 in FIG. 4. Arrow in the column-direction delay adder circuit 4 in FIG. 4 indicates a scanning direction in column direction. In the column-direction delay adder circuit 4, a delay time for a delay adding signal from each row-direction delay adder circuit is set so that the scanning direction viewed from the above direction coincides with the scanning direction of each beam received simultaneously in the column direction.

Figure 5:
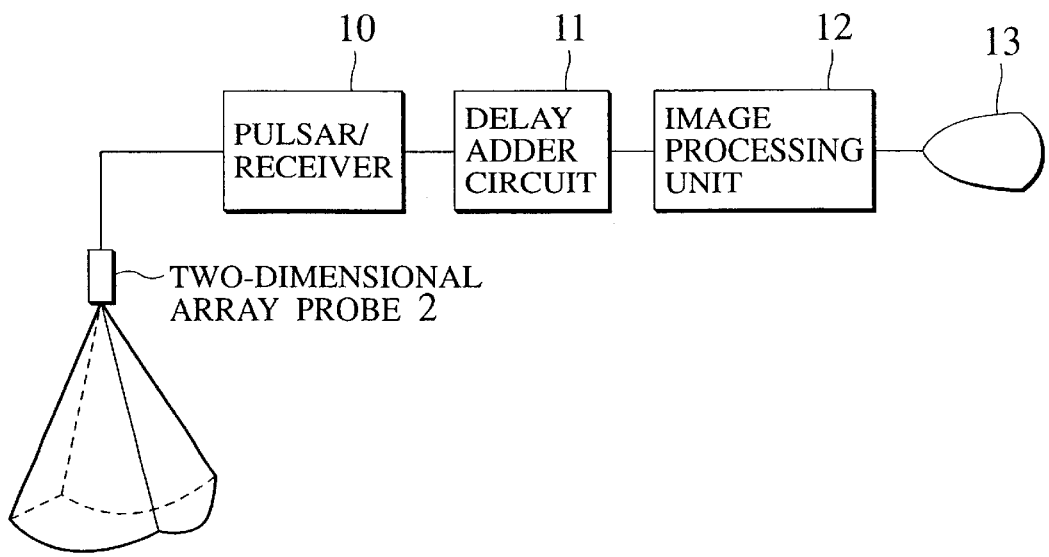
FIG. 5 is a block diagram for showing a configuration of the three-dimensional ultrasonic diagnostic apparatus relating to the first embodiment of the present invention.

FIG. 5 shows an overall configuration of the three-dimensional ultrasonic diagnostic apparatus relating to the first embodiment.

As shown in FIG. 5, the three-dimensional ultrasonic diagnostic apparatus relating to the first embodiment includes the two-dimensional array probe 2, a pulse receiver 10 for taking in detection signals from each transducer 1 of the two-dimensional array probe 2, a delay adder circuit 11 structured by the row-direction delay adder circuit 3 and the column-direction delay adder circuit 4, an image processing unit 12 for forming a three-dimensional image based on the reception signals from the delay adder circuit 11, and display unit 13 such as a cathode ray tube (CRT) or a liquid crystal display (LCD) or the like for displaying the three-dimensional image formed by the image processing unit 12.

Figure 6:
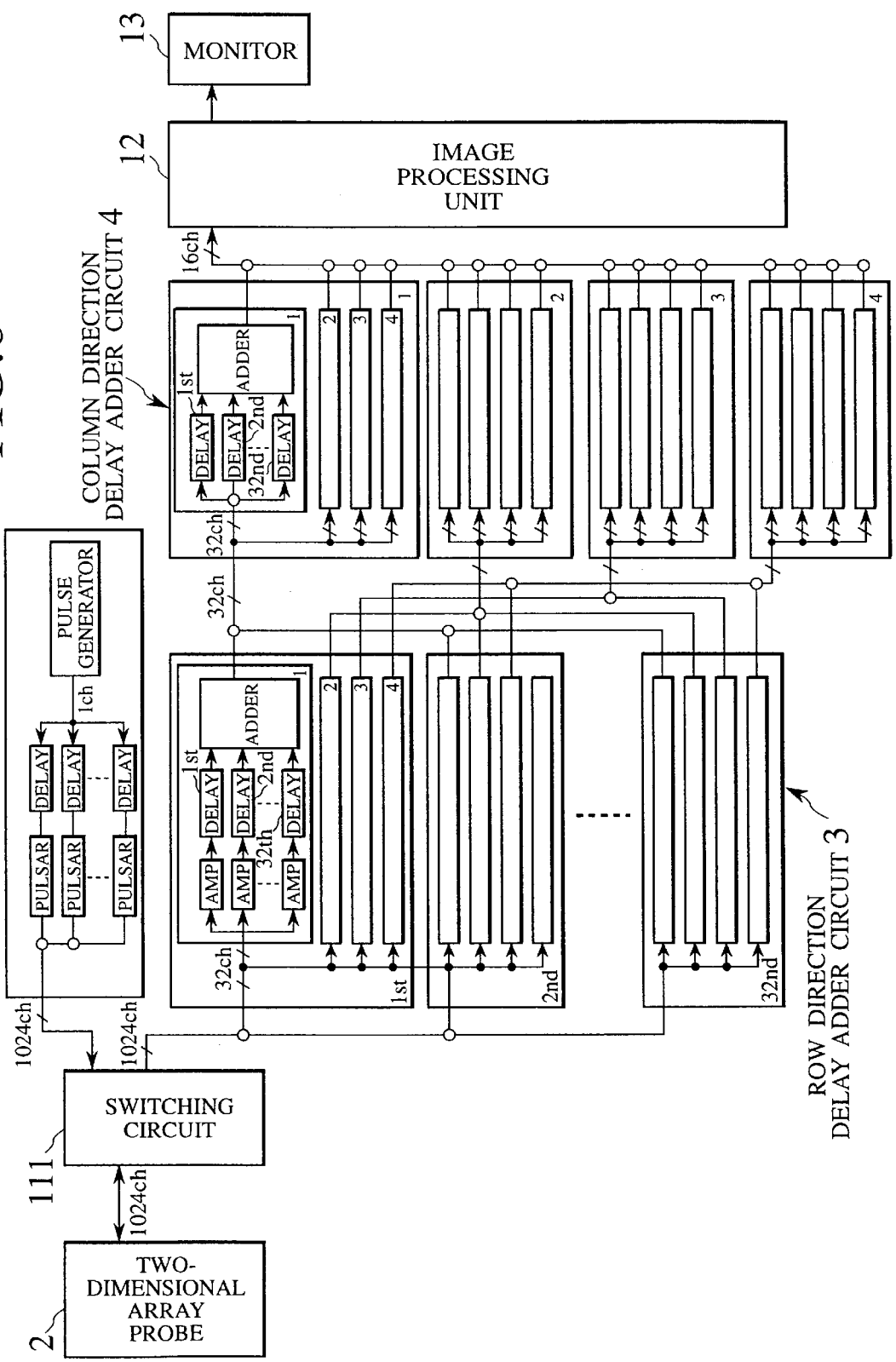
FIG. 6 is a block diagram for showing a partial configuration of the tree-dimensional ultrasonic diagnostic apparatus according to the first embodiment in detail.

FIG. 6 shows a block diagram showing detailed configuration of pulsar/receiver 10 and delay adder circuit 11 in FIG. 5 according to the first embodiment. As shown in FIG. 6, the row direction delay adder circuits 3 (first, second, . . . , 32$^{nd}$) are connected with two-dimensional array probe 2 via a switching circuit 111. The row direction delay adder circuit 3 comprises plural, e.g., 32 channel, amplifiers and delay circuits, and adder circuit, respectively. Each of the column direction delay adder circuits 4 (first, second, third and forth) comprises plural, e.g., 32 channel, delay circuits and adder circuit, that are connected to image processing unit 12.

Figure 1:
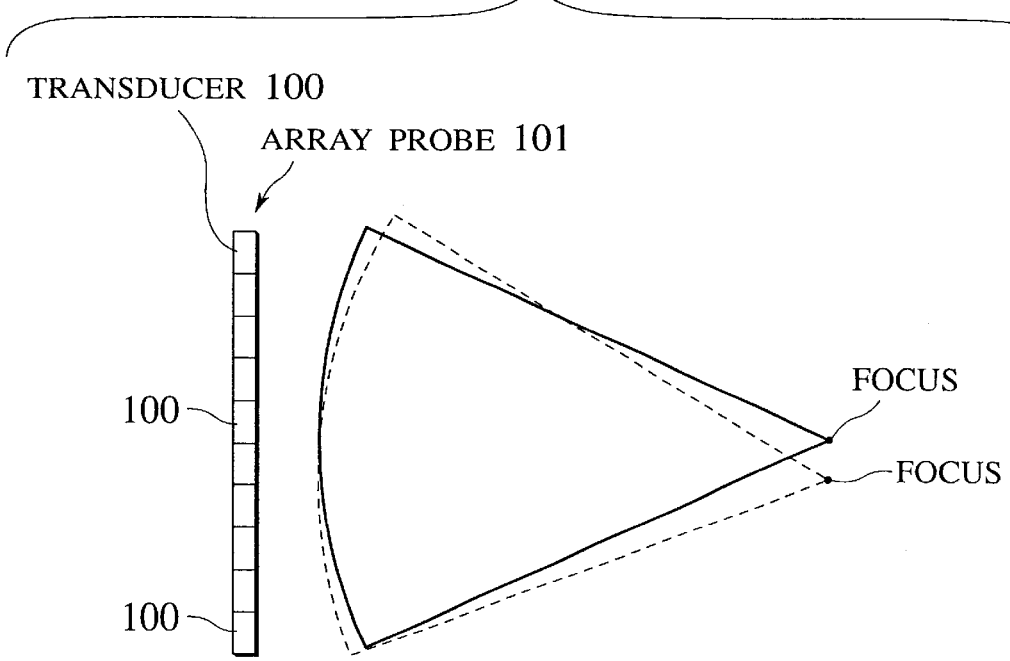
FIG. 1 is a view for explaining a one-dimensional array probe provided in a two-dimensional ultrasonic diagnostic apparatus according to a prior-art technique.
Figure 2:
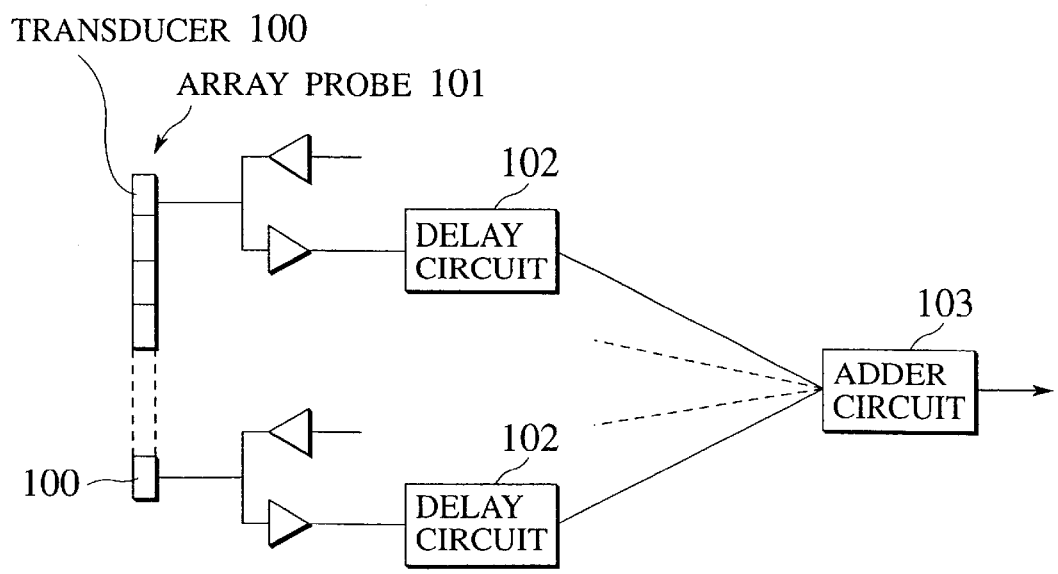
FIG. 2 is a view for explaining a configuration for carrying out a reception beam forming processing of the ultrasonic diagnostic apparatus according to the prior-art technique.
Figure 3:
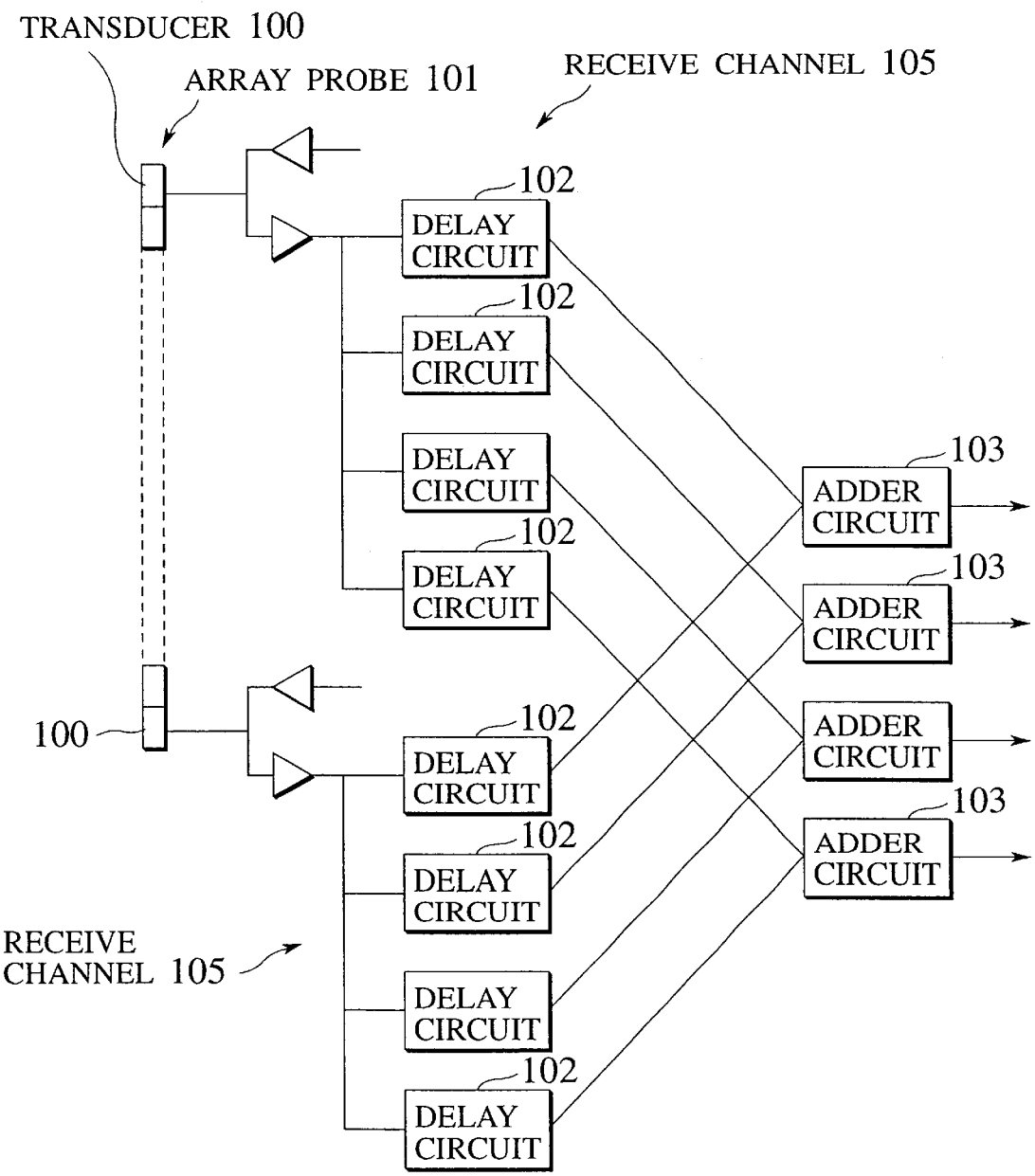
FIG. 3 is a view for explaining a simultaneous parallel reception processing of an ultrasonic diagnostic apparatus.

Next, the operation of forming the reception beams in the three-dimensional ultrasonic diagnostic apparatus relating to the first embodiment having the above-described structure will be explained next. At first, in FIG. 2, when a collection of a three-dimensional image of a subject has been started, an electric signal is supplied to each transducer 1 of the two-dimensional array probe 2. This electric signal is converted into a ultrasonic pulse signal by the transducer 1, and each transducer 1 emits an ultrasonic beam of a three-dimensional boxel shape after the conversion. By the emission of this ultrasonic beam, a reflection wave of the ultrasonic beam is generated from inside the subject. This reflection wave is detected by each transducer 1 of the two-dimensional array probe 2. The pulse receiver 10 takes in detection signals of the reflection wave detected by the transducers 1, and supplies these detection signals to the delay adder circuit 11.

Next, as shown in FIG. 4, the delay adder circuit 11 structured by the row-direction delay adder circuit 3 and the column-direction delay adder circuit 4 carries out the following delay add processing to the detection signals that are input. At first, the row-direction delay adder circuit 3 carries out a delay add processing to the detection signals detected by each transducer 1 in the row direction out of the detection signals from each transducer 1 of the two-dimensional array probe 2, and forms a time-series signal group.

In this case, it is assumed that the number of transducers in the row direction is "M", the number of parallel simultaneous receptions in the row direction is "K", and the number of transducers in the column direction is "N". The row-direction delay adder circuit 3 carries out a delay add processing by "M×K" times per one row. By this delay add processing, K signals which are the addition of signals of the same phase are generated per one row. In other words, the row-direction delay adder circuit 3 having N transducers in the column direction forms time-series signal groups of "N×K" signals in total. Accordingly, a total number of delay circuits required by the row-direction delay adder circuit 3 is calculated as "M×K×N".

Next, the column-direction delay adder circuit 4 carries out a delay add processing in the column direction to the time-series signal groups formed by the row-direction delay adder circuit 3.

In this case, it is assumed that the number of parallel simultaneous receptions is "L" in the column direction. The column-direction delay adder circuit 4 carries out a delay add processing by "L" times corresponding to the number of parallel simultaneous receptions in the column direction, to the time-series signal groups including "N×K" detection signals from the row-direction delay adder circuit 3. Accordingly, the number of delay circuits required by the column-direction delay adder circuit 4 is calculated as "N×K×L". The row-direction delay adder circuit 4 forms "K×L" reception signals and outputs them.

The column-direction delay adder circuit 4 supplies the delay add processed reception signals based on the three-dimensional scanning by the two-dimensional array probe 2, to the image processing unit 12 shown in FIG. 5.

In the manner as described above, the three-dimensional ultrasonic diagnostic apparatus relating to the first embodiment divides the detection signals detected by each transducer 1 of the two-dimensional array probe 2 into a row direction and a column direction, and carries out a delay add processing including a parallel simultaneous reception processing in each direction.

The total number of delay circuits required by the delay adder circuit 11 is obtained by the following formula:

$$(M \times K \times N) + (N \times K \times L) = N \times K \times (M+L)$$

As compared with the conventionally required number of delay circuits, this number can be decreased to:

$$(M+L)/(M \times L)$$

For example, it is assumed that the numbers of transducers in the row direction and the column direction are M and N respectively, and M and N are each 32, and that the numbers of parallel simultaneous receptions in the row direction and the column direction are K and L respectively, and K and L are each 4. In this case, the conventional three-dimensional ultrasonic diagnostic apparatus requires 32×32×4×4=16,384 delay circuits. On the other hand, as shown in FIG. 6, the three-dimensional ultrasonic diagnostic apparatus relating to the first embodiment can decrease this number to:

$$32 \times 4 \times (32+4) = 4,608 \text{ delay circuits}$$

In other words, the first embodiment makes it possible to decrease the required number of delay circuits to about one quarter of the conventionally required number.

When the "K×L" reception signals formed in the above-described manner have been supplied to the image processing unit 12 shown in FIG. 5, this unit forms a three-dimensional image based on the reception signals and supplies this three-dimensional image to the display unit 13. By this processing, the three-dimensional image of the subject taken in by the two-dimensional array probe 2 is displayed in real time through the display unit 13.

As explained above, the three-dimensional ultrasonic diagnostic apparatus relating to the first embodiment carries out a three-dimensional scanning in two stages in the delay adder circuit 11. Therefore, according to the first embodiment, it is possible to decrease substantially the number of delay circuits necessary for the parallel simultaneous reception processing used for the real-time display of the three-dimensional image. Accordingly, it is possible to reduce the manufacturing cost and power consumption of the three-dimensional ultrasonic diagnostic apparatus, and the real-time display of the three-dimensional ultrasonic diagnostic apparatus can be achieved more realistically.

In the above explanation of the first embodiment, at first the delay add processing is carried out to the detection signals of the transducers 1 in the row direction of the two-dimensional array probe 2, and then the delay add processing is carried out to the detection signals of the transducers 1 in the column direction. However, the first embodiment is not limited to this. It is needless to mention that the same effect as that obtained from the above process can also be obtained if it is arranged such that at first the delay add processing is carried out to the detection signals of the transducers 1 in the column direction of the two-dimensional array probe 2, and then the delay add processing is carried out to the detection signals of the transducers 1 in the row direction, for example.

Second Embodiment

Next, a three-dimensional ultrasonic diagnostic apparatus relating to a second embodiment of the present invention will be explained in detail below for only points different from the first embodiment with reference to the drawings.

The three-dimensional ultrasonic diagnostic apparatus according to the first embodiment is structured to decrease the required number of delay circuits by dividing the detection signals from the transducers 1 of the two-dimensional array probe 2 into detection signals in the row direction and the column direction and then by carrying out delay add processing to these detection signals respectively. On the other hand, according to the three-dimensional ultrasonic diagnostic apparatus relating to the second embodiment, at first the whole detection signals are divided into detection signals of each part, then a first delay add processing is carried out to these divided signals respectively, and finally a second delay add processing is carried out to the detection signals of each part to which the first delay add processing has been carried out. The second embodiment is different from the first embodiment in only the way of dividing the detection signals and the way of the delay add processing carried out to the divided detection signals. There will be explained hereinafter only these differences by omitting a duplicate explanation.

Figure 7:
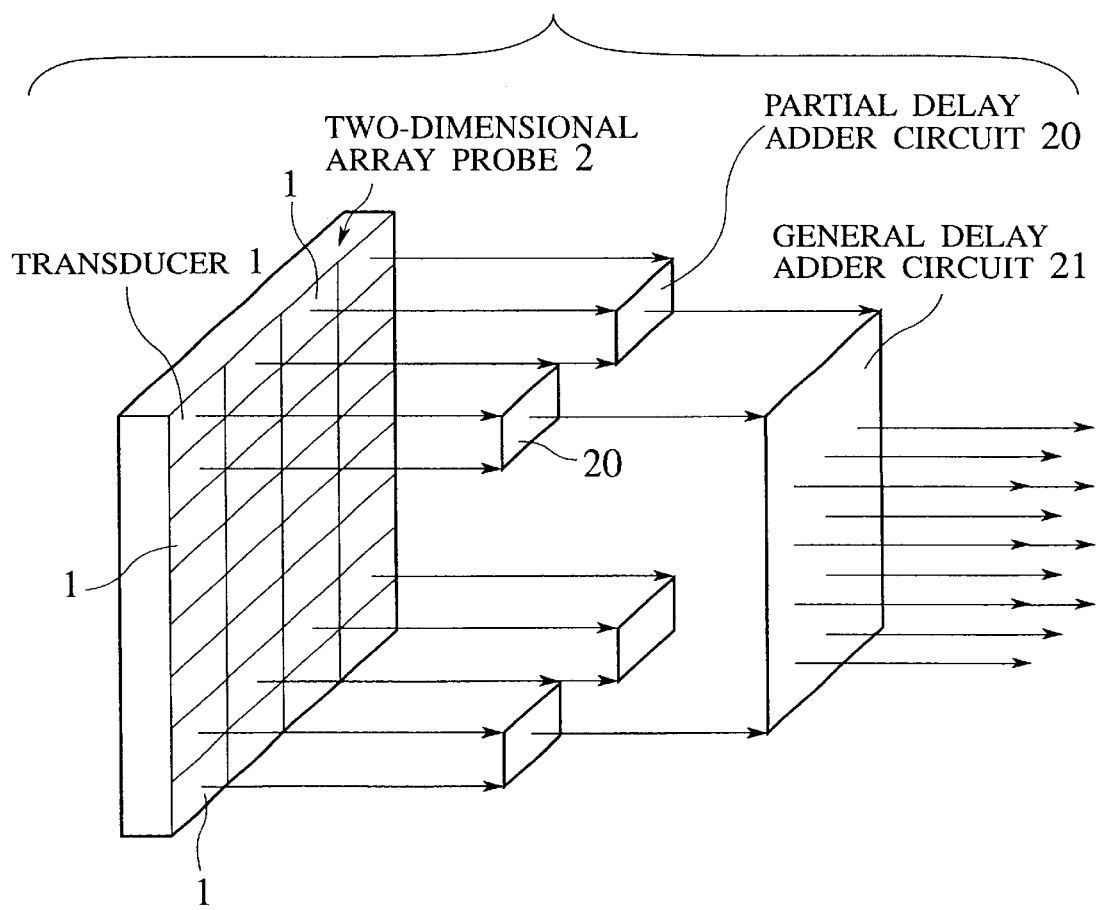
FIG. 7 is a view for explaining a configuration of a two-dimensional array probe and delay adder circuits of a three-dimensional ultrasonic diagnostic apparatus relating to a second embodiment of the present invention.

FIG. 7 shows a configuration of the three-dimensional ultrasonic diagnostic apparatus according to the second embodiment of the present invention.

As shown in FIG. 7, the three-dimensional ultrasonic diagnostic apparatus relating to the second embodiment includes a partial delay adder circuit 20 and a general delay adder circuit 21 for generating a plurality of delay adder signals corresponding to a plurality of scanning lines from respective signals from the partial delay adder circuit 20.

The partial delay adder circuit 20 carries out a delay add processing to detection signals of a predetermined part out of the whole detection signals from the transducers 1 of the two-dimensional array probe 2. This predetermined part is structured as a collection of detection signals positioned in adjacent area respectively. The partial delay adder circuit 20 obtains delay adding signals of the number corresponding to the number of channels smaller than the number of reception channels of the two-dimensional array probe 2. The general delay adder circuit 21 carries out a delay processing to the delay adding signals formed by this partial delay adder circuit 20 and adds these signals after being delayed. The general delay adder circuit 21 obtains a plurality of delay adding signals corresponding to a plurality of scanning directions from the delay adding signals output from the partial delay adder circuit 20.

Figure 8:
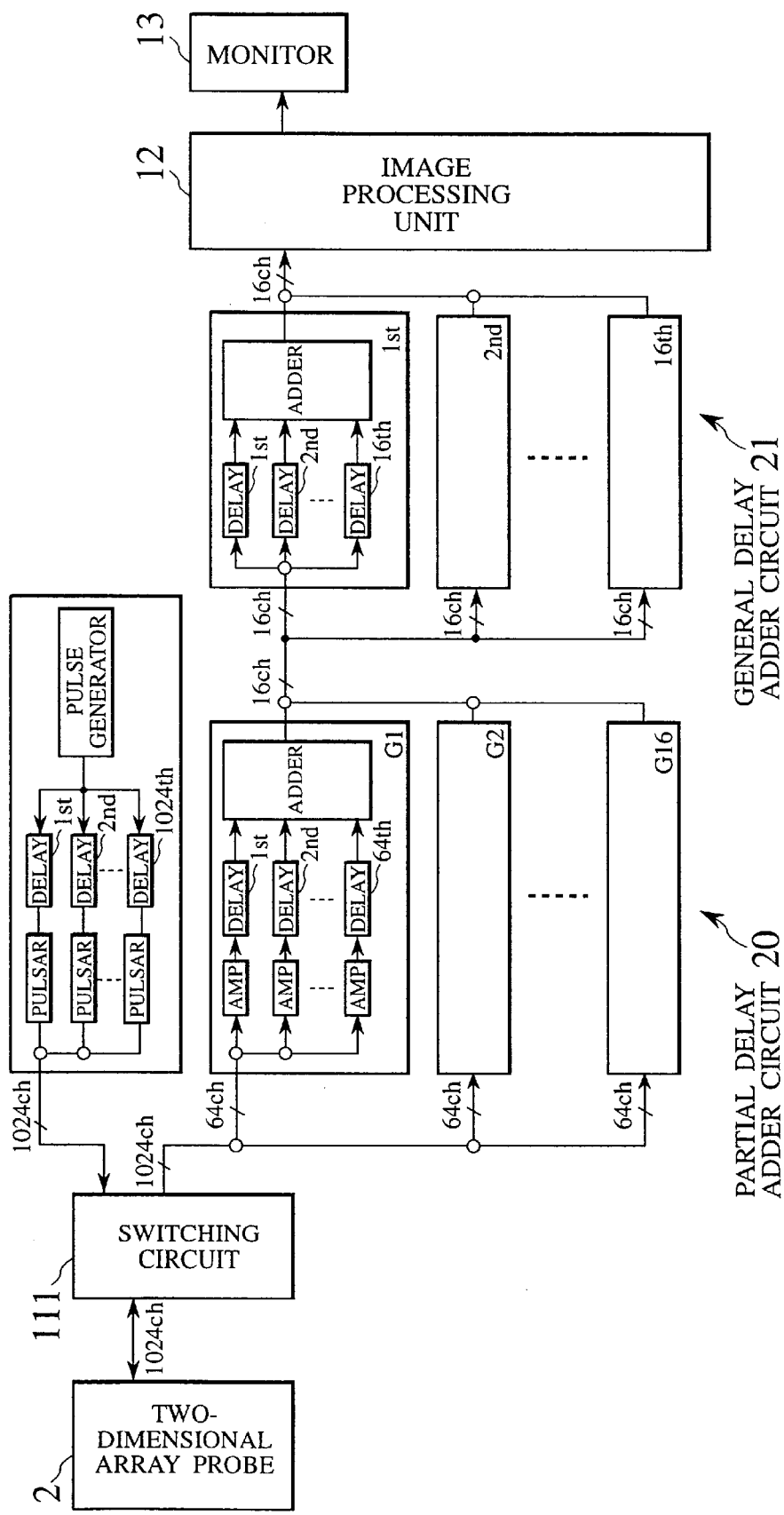
FIG. 8 is a block diagram for showing a partial configuration of the three-dimensional ultrasonic diagnostic apparatus according to the second embodiment in detail.

FIG. 8 shows a block diagram showing detail configuration of the pulsar/receiver 10 and delay adder circuit 11 according to the second embodiment. As shown in FIG. 8, the partial delay adder circuits 20 (first, second, . . . , 16th) are connected with two-dimensional array probe 2 via a switching circuit 111. The partial delay adder circuit 20 comprises plural, e. g., 64 channel, amplifiers and delay circuits, and adder circuit, respectively. Each of the general delay adder circuits 21 (first, second, . . . , 16th) comprises plural, e.g., 16 channel, delay circuits and adder circuit, that is connected to image processing unit 12.

The partial delay adder circuit 20 also determines an approximate direction of beam scanning lines by applying a delay add processing to the partial detection signals. The general delay adder circuit 21 adjusts approximated directions of the beam scanning lines by applying a delay add processing to the delay adding signals output from a plurality of partial delay adder circuits 20.

The directions of these scanning lines are controlled by the setting of delay times of the respective delay circuits.

To be more specific, in the partial delay adder circuit 20, delay time of the reception signal to each transducer is set so that a combined ultrasonic directivity formed by all transducer elements that are to be delay added while receiving becomes almost parallel with a ultrasonic directivity formed by each partial delay adder circuit 20 received parallel simultaneously.

Figure 9:
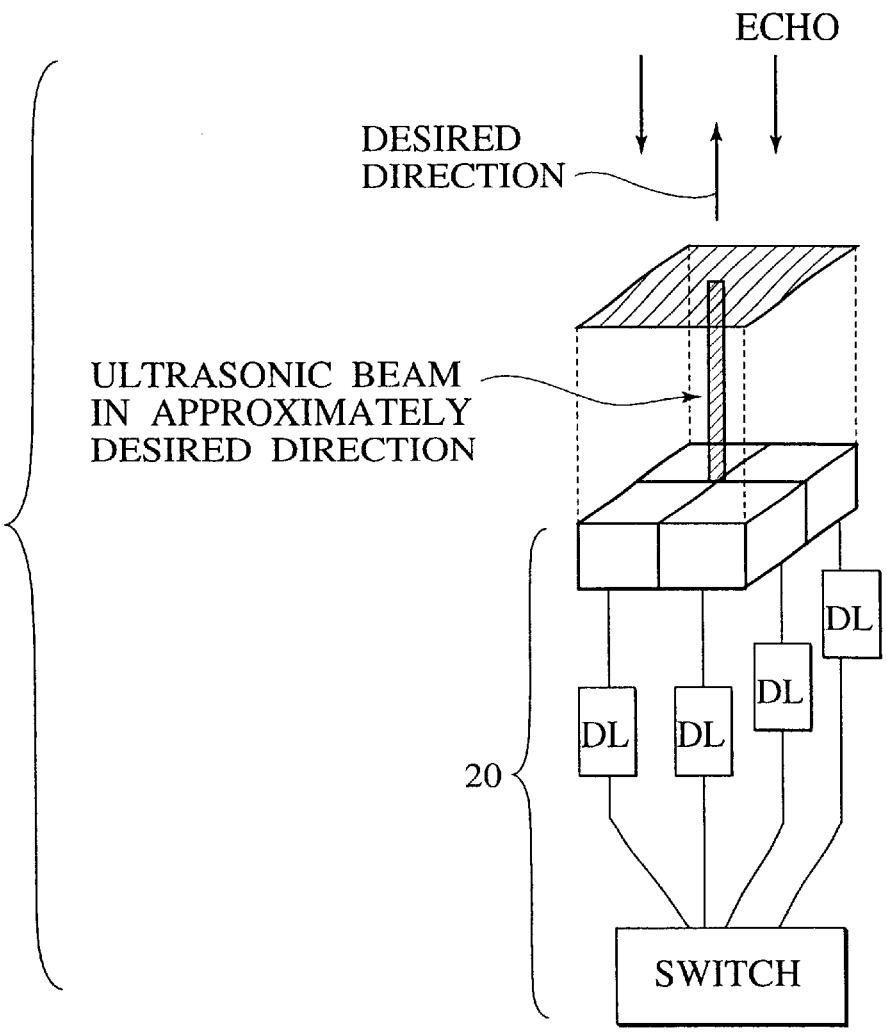
FIG. 9 is a view for explaining a delay time setting for a partial delay adder circuit in a second embodiment.
Figure 10:
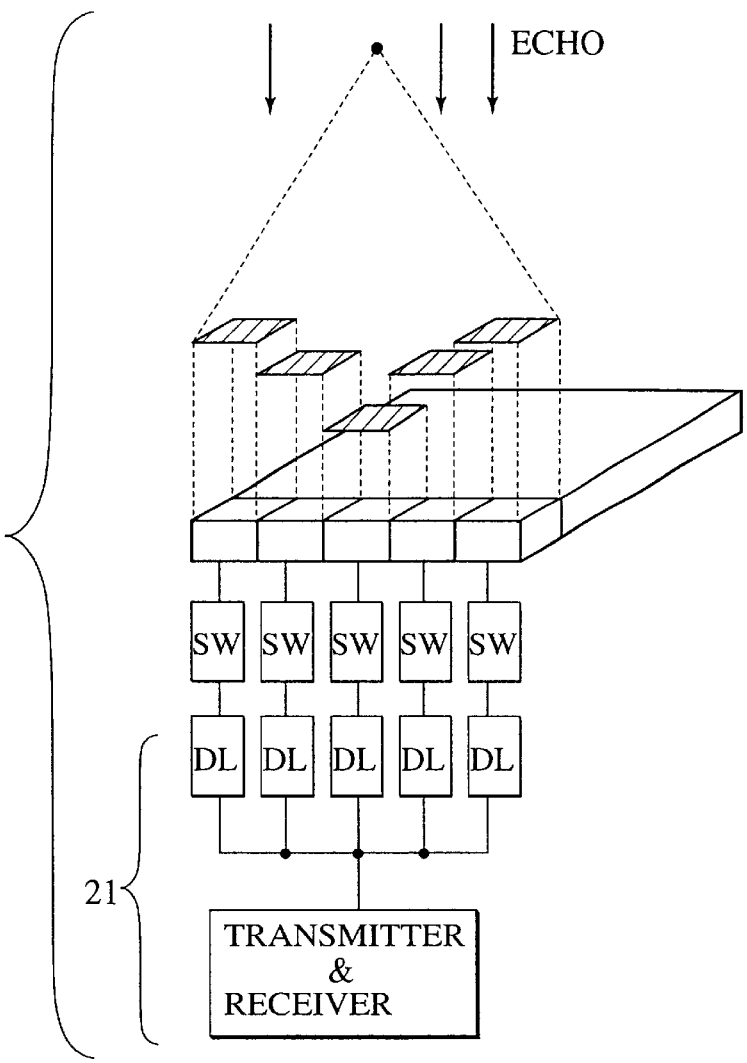
FIG. 10 is a view for explaining a relationship between a partial delay adder circuit and a general delay adder circuit in a second embodiment.
Figure 11:
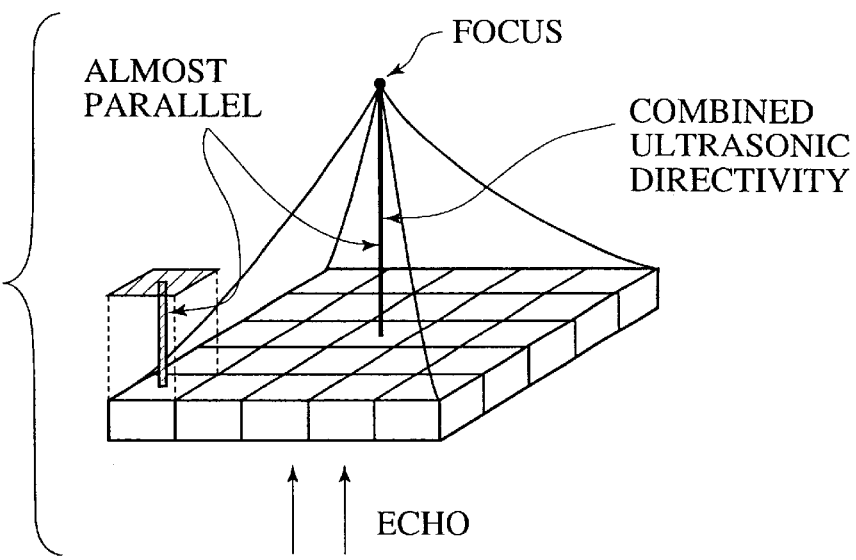
FIG. 11 is a view for explaining a delay time setting for a partial delay adder circuit in a second embodiment.

FIG. 9 shows the ultrasonic directivity formed by each partial delay adder circuit 20 while receiving. In each partial delay adder circuit 20, a focus of receiving ultrasonic wave is not formed yet, so that a receiving signal of ultrasonic beams is not converged sufficiently. As shown in FIG. 10, the delay time for receiving ultrasonic to be set in each partial delay adder circuit 20 differs each other so as to form one focus in general delay adder circuit 21. Therefore, as shown in FIG. 11, the ultrasonic directivity formed by each partial delay adder circuit 20 become almost parallel with the combined ultrasonic directivity formed by all transducer elements.

On the other hand, in the general delay adder circuit 21, delay time of the receiving signals delay added by the general delay adder circuit 21 is set so as to form corresponding scanning lines along scanning direction for ultrasonic receiving. In the second embodiment, the scanning directions of the scanning lines include two directions of row and column directions.

Figure 12C:
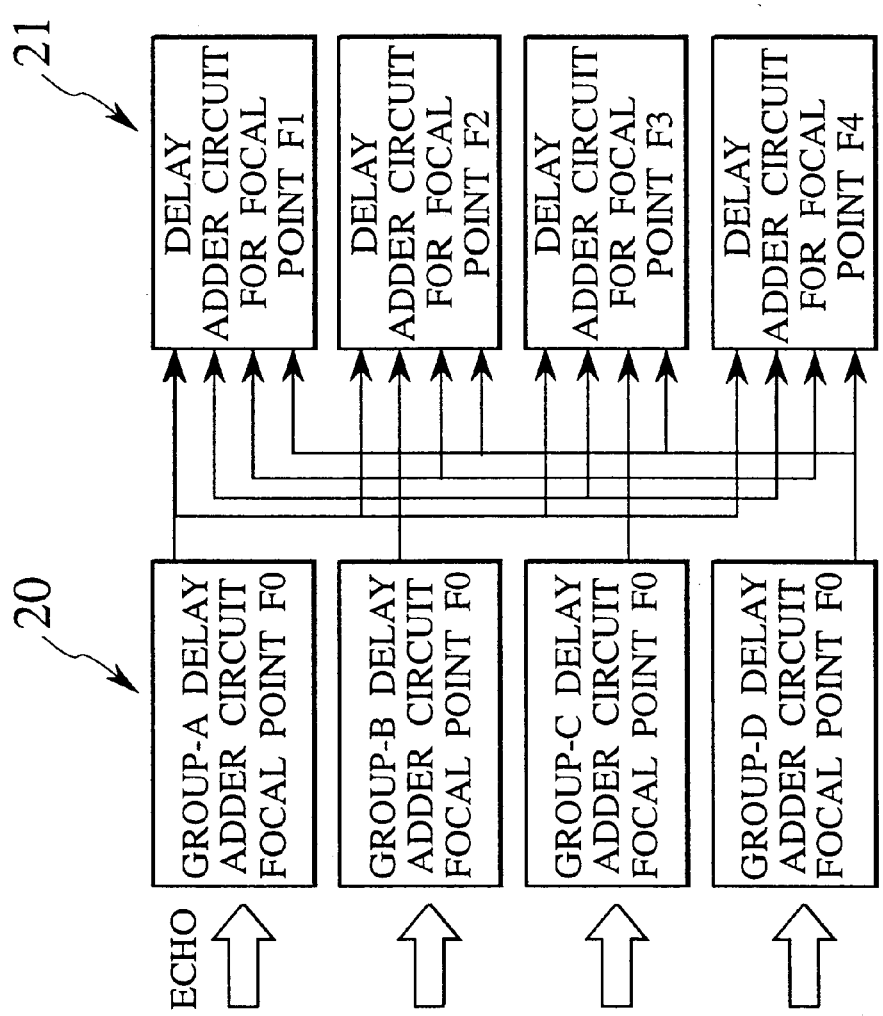
FIGS. 12A to C are views for explaining a delay time setting for a partial delay adder circuit in the second embodiment.
Figure 12A:
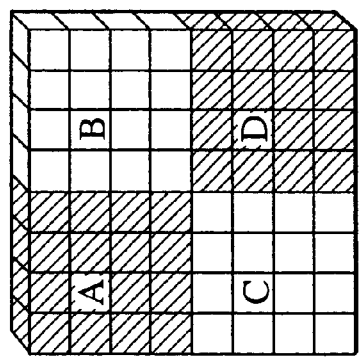
Figure 12B:
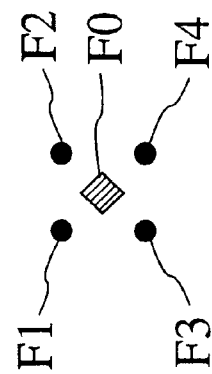

FIGS. 12A to C show views for explaining the delay time setting for the partial delay adder circuit according to the second embodiment.

A delay time Ti to be set for output signal of I-th element in partial, e.g., group-A, delay adder circuit (for focal point F0) is expressed as follows:

$$Ti=T+(-|rF-ri|+|rF-rA|)/c \quad (1)$$

Where rA denotes the center position vector of group-A, ri denotes the position vector of I-th element, rF denotes the position vector of focal point F0, c indicates the sonic speed and T denotes a constant.

The delay time expressed by above formula (1) corresponds delay time in which the beam from each element in each group is to be converged onto the focal point F0.

On the other hand, a delay time T1A to be set for output signal from group-A delay adder circuit in delay adder circuit for focal point F1 is written as follows:

$$T1A=-|rf1-rA|/c \quad (2)$$

Where rf1 denotes the position vector of focal point F1.

The output signals from each group (partial) delay adder circuit are delayed by the delay time that the above formula expresses. The delay process expressed by above formula corresponds to that in which the beam from each element is to be converged onto the focal point F1, where each group A to D is assumed as one element. The output signals from group-B delay adder circuit are delayed by the delay time expressed by above formula in which rA is replaced with rB. The portion "|rF-rA|/c" in formula (1) may be carried out in second delay adding process. Note that delay adding process described above is an exemplary case, and other same delay adding process can be employed in the second embodiment.

Next, the operation of forming reception beams in the three-dimensional ultrasonic diagnostic apparatus relating to the second embodiment will be explained below.

In the three-dimensional ultrasonic diagnostic apparatus according to the second embodiment, reflection waves are detected by the transducers 1 of the two-dimensional array probe 2. First, the partial delay circuit 20 carries out a delay add processing to detection signals detected by each transducer 1. As explained above, the partial delay adder circuit 20 carries out a delay add processing to the detection signals of each predetermined partial transducer group so that the combined ultrasonic directivity for receiving formed by all transducer elements to be delay added becomes almost parallel with the ultrasonic directivity of each channel received parallel simultaneously.

The delay adding signals output from the each partial delay adder circuits 20 are supplied to the general delay adder circuit 21.

Next, the general delay adder circuit 21 carries out a delay add processing to the delay adding signals output from the each partial delay adder circuits 20 so that the delay adder signals corresponding to the scanning lines received parallel simultaneously, thereby to form reception signals. The reception signals formed are supplied, to the image processing unit 12 shown in FIG. 5.

Based on the above-described processing, according to the second embodiment, the partial delay adder circuit 20 carries out a delay add processing to each detection signal of each part positioned near by. A delay add processing taking into account a parallel simultaneous reception processing is carried out to the delay add signals obtained. Accordingly, the general delay adder circuit 21 carries out a parallel simultaneous reception processing to the signals corresponding to the number of the channels smaller than an actual number of the reception channels. Therefore, a required number of delay circuits can be decreased.

It is assumed, for example, that the total number of channels held by the pulse receiver 10 is 1,024 (that is, 32×32), the number of parallel simultaneous receptions is 16 (4×4), and the number of channels per one group of channel groups corresponding to partial detection signal groups detected by each partial delay adder circuit 20 is 16. In this case, 1,024 channels are necessary for forming all the first partial detection signals. In this time, the number of channels is limited to a small number as follows in this case:

1,024 channels/16 channels=64 channels

Therefore, the following number of channels is necessary for carrying out a parallel simultaneous reception processing to the obtained partial detection signal groups:

64 channel×16=1,024 channels

Accordingly, the three-dimensional ultrasonic diagnostic apparatus relating to the second embodiment can be achieved by delay circuits by the number of (1,024+1,024) channels, that is, 2,048 channels in total, as shown in FIG. 8. On the contrary, the conventional three-dimensional ultrasonic diagnostic apparatus requires delay circuits by the number of (1,024×16) channels, totaling 16,384 channels. Therefore, the three-dimensional ultrasonic diagnostic apparatus relating to the second embodiment can decrease the required number of delay circuits to ⅛ of that required conventionally.

In summary, as explained above, the three-dimensional ultrasonic diagnostic apparatus relating to the present invention carries out delay add processing including parallel simultaneous reception processing, to the detection signals in a plurality of stages. Accordingly, it is possible to decrease substantially the number of delay units necessary for the parallel simultaneous reception processing to be used for achieving a real-time display of a three-dimensional image. As a result, it is possible to decrease the manufacturing cost and power consumption respectively of the apparatus.

Various modifications will become possible for those skilled in the art after receiving the teachings of the present disclosure without departing from the scope thereof. It is intended, therefore, that all matter contained in the foregoing description and in the drawings shall be interpreted as illustrative only not as limitative of the invention.

What is claimed is:

1. An ultrasonic diagnostic apparatus for forming a three-dimensional image using a reflection wave of an ultrasonic beam, comprising:

a three-dimensional ultrasonic scanning unit for carrying out a three-dimensional ultrasonic scanning by a plurality of ultrasonic transducers arranged two-dimensionally and forming detection signals corresponding to reflection waves reflected from a subject that are detected by the transducers;

a first delay add processing unit for dividing detection signals from all the transducers into a predetermined plurality of partial signal groups and carrying out delay add processing to each of the divided partial signal groups to form a first delay adding signal;

a second delay add processing unit for carrying out a delay add processing to the first delay adding signal output from the first delay add processing unit to form a second delay adding signal; and an image processing unit for reconstructing a three-dimensional image according to the second delay adding signal output from the second delay add processing unit.

2. The ultrasonic diagnostic apparatus according to claim 1, wherein the first delay add processing unit divides detection signals from all the transducers into a plurality of partial signal groups in either a row direction or a column direction of the array of the transducers, and the second delay add processing unit divides the first delay adding signal output from the first delay add processing section into a plurality of partial signal groups in the other direction of the row direction or the column direction, and carries out a delay add processing to the respective divided partial signal groups.

3. The ultrasonic diagnostic apparatus according to claim 2, wherein the first and second delay add processing units respectively include:

a delay circuit provided by a plurality of number for one reception channel and for forming detection signals whose phases are mutually different; and an adder circuit for adding detection signal groups of the same phase out of detection signal groups output from the delay circuit and for outputting a delay adding signal.

4. The ultrasonic diagnostic apparatus according to claim 2, wherein the first delay add processing unit delays the partial signal group so that a scanning direction observed from one of the row direction and the column direction coincides with a scanning direction of a plurality of scanning lines corresponding to one reception channel, and the second delay add processing unit delays the partial signal group so that a scanning direction observed from the other direction of either the row direction or the column direction coincides with a scanning direction of a plurality of scanning lines corresponding to one reception channel.

5. The ultrasonic diagnostic apparatus according to claim 1, wherein the first delay add processing unit divides detection signals from all the transducers into a plurality of partial signal groups which are located in adjacent area respectively, and the second delay add processing section carries out a delay add processing to the first delay adding signals.

6. The ultrasonic diagnostic apparatus according to claim 5, wherein the first delay add processing unit forms the first delay adding signals according to detection signal groups detected in channel groups whose number of channels is smaller than the number of all reception channels corresponding to all the transducers.

7. The ultrasonic diagnostic apparatus according to claim 5, wherein the first and second delay add processing units respectively include:

a delay circuit provided by a plurality of number for one reception channel and for forming detection signals whose phases are mutually different; and an adder circuit for adding detection signal groups of the same phase out of detection signal groups output from the delay circuit and for outputting a delay adding signal.

8. The ultrasonic diagnostic apparatus according to claim 5, wherein the first delay add processing unit delays the partial signal group so that a combined ultrasonic directivity formed by all the transducers becomes almost parallel with ultrasonic directivity formed by each partial delay add processing unit respectively, and the second delay add processing unit delays the partial signal group so as to form corresponding scanning lines with respect to scanning directions.

9. The ultrasonic diagnostic apparatus according to claim 6, wherein the first and second delay add processing units respectively include:

a delay circuit provided by a plurality of number for one reception channel and for forming detection signals whose phases are mutually different; and an adder circuit for adding detection signal groups of the same phase out of detection signal groups output from the delay circuit and for outputting a delay adding signal.

10. The ultrasonic diagnostic apparatus according to claim 6, wherein the first delay add processing unit delays the partial signal group so that a combined ultrasonic directivity formed by all the transducers becomes substantially parallel with ultrasonic directivity formed by each partial delay add processing unit respectively, and the second delay add processing unit delays the partial signal group so as to form corresponding scanning lines with respect to scanning directions.

11. The ultrasonic diagnostic apparatus according to claim 1, wherein the first and second delay add processing units respectively include:

a delay circuit provided by a plurality of number for one reception channel and for forming detection signals whose phases are mutually different; and an adder circuit for adding detection signal groups of the same phase out of detection signal groups output from the delay circuit and for outputting a delay adding signal.

12. An ultrasonic diagnostic apparatus for forming a three-dimensional image using a reflection wave of an ultrasonic beam, comprising:

a three-dimensional ultrasonic scanning unit for carrying out a three-dimensional ultrasonic scanning by a plurality of ultrasonic transducers arranged two-dimensionally and forming detection signals corresponding to reflection waves reflected from a subject that are detected by the transducers;

a first delay processing unit for dividing detection signal from all the transducers into a plurality of partial signal groups in one direction of either a row direction or a column direction of the array of the transducers and forming a plurality of signals in the one direction with mutually different phases for one reception channel from each of the divided partial signal groups;

a first add processing unit for adding detection signal groups of the same phase out of the detection signal groups output from the first delay processing section to form a first delay adding signal;

a second delay processing unit for forming a delay signal in the other direction with mutually different phases for one reception channel, out of the first delay adding signal output from the first add processing unit;

a second add processing unit for forming a second delay adding signal by adding delay signal groups of the same phase out of the delay signals output from the second delay processing unit; and an image processing unit for reconstructing a three-dimensional image according to the second delay adding signal output from the second add processing unit.

13. An ultrasonic diagnostic apparatus for forming a three-dimensional image using are reflection wave of an ultrasonic beam, comprising:

a three-dimensional ultrasonic scanning unit for carrying out a three-dimensional ultrasonic scanning by a plurality of ultrasonic transducers arranged two-dimensionally and for forming detection signals corresponding to reflection waves reflected from a subject that are detected by the transducers;

a plurality of first delay processing units for dividing detection signal from all the transducers into a plurality of partial signal groups in adjacent area and for forming a plurality of signals with mutually different phases for one reception channel from each of the divided partial signal groups;

a plurality of first add processing units for adding detection signal groups of the same phase out of the detection signal groups output from the first delay processing section to form a first delay adding signal;

a second delay processing unit for forming a delay signal with mutually different phases for one reception channel, out of the first delay adding signal output from the first add processing unit;

a second add processing unit for forming a second delay adding signal by adding delay signal groups of the same phase out of the delay signals output from the second delay processing unit; and an image processing unit for reconstructing a three-dimensional image according to the second delay adding signal output from the second add processing unit.

* * * * *